United States Patent [19]
Wicks et al.

[11] Patent Number: 6,090,541
[45] Date of Patent: Jul. 18, 2000

[54] METHOD AND DEVICE FOR DETECTING BACTERIOPHAGE USING CONTRAST-COLORING AND PRECIPITABLE DYES

[75] Inventors: James H. Wicks, Oakdale; Gary E. Krejcarek, White Bear Lake; Michael G. Williams, Vadnais Heights, all of Minn.

[73] Assignee: 3M Innovative Properties Company, St. Paul, Minn.

[21] Appl. No.: 09/350,978

[22] Filed: Jul. 9, 1999

Related U.S. Application Data

[62] Division of application No. 08/844,145, Apr. 18, 1997, Pat. No. 5,958,675.

[51] Int. Cl.[7] .............................. C12Q 1/70; C12Q 1/04; C12M 1/34
[52] U.S. Cl. ............................ 435/5; 435/34; 435/287.1; 435/288.4
[58] Field of Search .................................. 435/5, 29, 34, 435/287.1, 288.4

[56] References Cited

U.S. PATENT DOCUMENTS

| | | | |
|---|---|---|---|
| 4,565,783 | 1/1986 | Hansen et al. | 435/299 |
| 4,797,363 | 1/1989 | Teodorescu et al. | 435/235 |
| 5,089,413 | 2/1992 | Nelson et al. | 435/254 |
| 5,137,812 | 8/1992 | Matner | 435/38 |
| 5,210,022 | 5/1993 | Roth et al. | 435/34 |
| 5,232,838 | 8/1993 | Nelson et al. | 435/30 |
| 5,358,854 | 10/1994 | Ferguson | 435/14 |
| 5,364,766 | 11/1994 | Mach et al. | 435/34 |
| 5,409,838 | 4/1995 | Wickert | 436/8 |
| 5,443,963 | 8/1995 | Lund | 435/34 |
| 5,447,836 | 9/1995 | Wolber et al. | 435/4 |
| 5,462,860 | 10/1995 | Mach | 435/34 |
| 5,498,525 | 3/1996 | Rees et al. | 435/29 |
| 5,527,667 | 6/1996 | Ijzerman et al. | 435/5 |
| 5,723,330 | 3/1998 | Rees et al. | 435/252.3 |
| 5,840,308 | 11/1998 | Jassim et al. | 424/195.1 |
| 5,958,675 | 9/1999 | Wicks et al. | 435/5 |

FOREIGN PATENT DOCUMENTS

| | | |
|---|---|---|
| 0 398 703 A1 | 11/1990 | European Pat. Off. . |
| WO 95/05483A1 | 2/1995 | WIPO . |
| WO 98/48042 | 10/1998 | WIPO . |

OTHER PUBLICATIONS

"Standard Test Method for Coliphages in Water[1]," ASTM Designation: D4201—82 (Reapproved 1989).
Emergency Standard Test Method for Resistance of Protective Clothing Materials to Penetration by Blood–Borne Pathogens Using Viral Penetraion as a Test System[1,2], ASTM Designation: ES 22– 92, 1991.

Ijerman et al., "Improved Method for Coliphage Detection Based on β–galactosidase Induction," *Journal of Virological Methods*, vol. 40 (1992) pp. 31–36.

Ijzerman et al., "A Liquid, Colorimetric Presence–Absence Coliphage Detection Method," *Journal of Virological Methods*, vol. 45 (1993) pp. 229–234.

Ijzerman et al., "Field Evaluation of Two Colorimetric Coliphage Detection Methods," *Appied and Environmental Microbiology*, Mar., 1994, pp. 826–830.

Hurst et al., "Differential Effect of Tetrazolium Dyes Upon Bacteriophage Plaque Assay Titers," *Applied and Environmental Microbiology*, Sep., 1994, pp. 3462–3465.

Patent Abstracts of Japan, vol. 15, No. 341 (117 C 863), 1991; & JP,A,3–133399 (Mitsubishi Heavy Ind. Ltd), abstract.

Patent Abstracts of Japan, vol. 14, No. 318 (13 C 738), 1990; & JP,A,2–110000 (Mitsubishi Heavy Ind. Ltd), abstract.

*Primary Examiner*—David M. Naff
*Attorney, Agent, or Firm*—James A. Rogers

[57] ABSTRACT

The use of a precipitable dye and a contrast-coloring dye together enhance visualization of plaques in confluent lawns of bacteria in bacteriophage and bacteria assays. A test sample suspected of containing a bacteriophage is combined with bacteria capable of replicating the bacteriophage, and applied to a water-proof surface to form a support for bacterial growth. The support is provided with the contrast-coloring dye and precipitable dye, and nutrients and salts capable of supporting growth of the bacteria. A lawn of bacteria is formed on the support, and plaques detected on the lawn indicate presence of the bacteriophage. The plaques contain a precipitate formed by enzymatic cleavage of the precipitable dye by an enzyme of the bacterial lawn. A similar procedure is used for detecting bacteria, except that a test sample suspected of containing a bacteria is combined with bacteriophage capable of replicating in the bacteria, and plaques detected indicate presence of the bacteria. The bacteriophage and bacteria assays are carried out with a disposable device containing at least one well having a water-proof surface and a depth of about at least 5 millimeters. A hydratable material containing the contrast-coloring dye and precipitable dye is positioned on the surface. The well may contain substantially vertical sides with a removable cover resting on top of the sides.

37 Claims, 1 Drawing Sheet ial patent application No. 2055741, published May 19, 1971,
METHOD AND DEVICE FOR DETECTING BACTERIOPHAGE USING CONTRAST-COLORING AND PRECIPITABLE DYES This is a divisional of application Ser. No. 08/844,145 filed Apr. 18, 1997, now U.S. Pat. No. 5,958,675.

FIELD OF THE INVENTION

This invention relates to methods for culturing microorganisms and to methods for detecting viruses. In particular, this invention relates to methods and devices for detecting bacteriophages.

BACKGROUND OF THE INVENTION

The quantitation of bacterial viruses is important to a number of disciplines. For example, the presence of bacteriophage in a sample is one method for detecting the presence or absence of bacteria in that particular sample. The presence of these indicator organisms is widely used to assess bacterial contamination in various products. Both water and food quality are defined, in part, by the presence or absence of members of the "coliform" group, including the presence of *Escherichia coli* in a sample. Coliforms include members of the Enterobacteriaceae group and have the ability to ferment lactose with gas production. The genera Citrobacter, Enterobacter, Klebsiella and Escherichia are generally listed members of the coliform group.

In addition, bacteriophage are used in molecular studies for gene manipulation, as evidenced by the extensive commercial use of genetically modified bacteriophage vectors. Genetically modified bacteriophage are available from commercial suppliers including, but not limited to, Stratagene (La Jolla, Calif.), Invitrogen (San Diego, Calif.) and New England Biolabs (Beverly, Mass.). Rapid quantitation of bacteriophage is important to expediting biotechnology research.

Lytic bacterial viruses replicate within the bacterial cell resulting in bacterial lysis to release virus progeny. Lytic bacteriophages form substantially clear plaques on a lawn of bacteria (i.e., a confluent covering of bacteria). Nonlytic bacteriophages may not lyse a cell. Instead, the rate of bacterial cell growth slows and the viruses form turbid plaques on a bacterial lawn.

Standard petri-plate type assays for bacteriophage are known in the art. In these assays, agar-containing media is poured into petri-plates. A sample suspected of containing bacteriophage or known to contain bacteriophage is combined with bacteria susceptible to infection by that type of bacteriophage in a top agar-containing media. The top agar is poured over the agar plate, allowed to solidify, and the plate is incubated until areas of bacterial lysis, termed plaques, are observed on the lawn of bacteria. The plaques are counted and the number of plaques is adjusted in view of the original sample dilution to obtain the concentration of bacteriophage in the sample. Examples of these methods are disclosed, for example, in Sambrook et al. (*Molecular Cloning: A Laboratory Manual*, 1989, Cold Spring Harbor Laboratory Press, Cold Spring Harbor, N.Y.). Results are generally expressed as plaque forming units (pfu)/ml.

Standard petri-plate bacteriophage assays are tedious and cumbersome and often produce inaccurate results because it is often difficult to see all of the virus plaques on the bacterial lawn. Moreover, standard agar-containing petri-plates have a relatively short shelf half-life. The agar can dry out and the plates generally require refrigeration. A ready-to-use device to facilitate bacteriophage quantitation is needed.

The prior art has provided several devices that are useful for assaying liquid samples for bacteria and molds. German patent application No. 2055741, published May 19, 1971, discloses a microbiological growth medium comprised of an inert card or strip coated with a dry-gelled medium. U.S. Pat. Nos. 4,565,783, 5,443,963, 5,462,860, and 5,232,838 provide a culture media device comprising a cold-water soluble dry powder containing a gelling agent and microbial growth nutrients coated on a water-proof surface and examples of these devices are commercially available as "PETRI-FILM" devices from Minnesota Mining and Manufacturing Co., St. Paul, Minn. In these references, a transparent, read-through cover sheet is positioned on top of a surface. The application of a liquid sample to the device hydrates the gelling agent on the surface to form a gelatinous medium for growing microorganisms. These references provide flat growing surfaces with covers that contact the surface containing the organism. Such devices are not suitable for quantitating bacteriophage since direct contact of a cover with a bacterial lawn infected with bacteriophage would smear the plaques and produce inaccurate results for bacteriophage quantitation.

U.S. Pat. No. 5,089,413 discloses a device for growing microorganisms including aerobic microorganisms such as mold. The device employs an air permeable membrane to permit the growth of aerobic organisms. A spacer is disclosed in the device to define the growth region and confine an aqueous sample to the growth region of the medium. In this patent, like those cited above, the cover is designed to contact the growth surface to disperse the sample across the growth surface of the device.

There remains a need for a device and a method to detect bacteriophage quickly and easily without requiring significant preparation steps to produce and maintain a supply of solid media coated plates suitable for bacteriophage replication on a lawn of bacteria.

SUMMARY OF THE INVENTION

This invention involves the use of a precipitable dye and a contrast-functioning dye together to enhance the visualization of bacteriophage-derived plaques in confluent lawns of bacteria in bacteriophage assays.

In one aspect of this invention the invention relates to a method for detecting bacteriophage comprising the steps of: combining a test sample comprising bacteriophage with bacteria capable of supporting replication of the bacteriophage to form a liquid sample; applying the liquid sample of the combining step to a water-proof surface, where the surface with the liquid sample comprises at least one contrast-coloring dye, at least one precipitable dye, and nutrients and salts capable of supporting growth of the bacteria, wherein a precipitate of the precipitable dye is formed from the enzymatic cleavage of the precipitable dye by an enzyme from the liquid sample; forming a lawn of bacteria on a support positioned on the surface; and detecting plaques formed on the surface of the bacterial lawn. In one embodiment of this method, the liquid sample comprises a solidifiable support in liquid form. Alternatively the surface of the applying step can comprise a hydratable solidifying support. In one embodiment, the surface of the applying step comprises a semi-solid support. The support of this invention can include a variety of gelling agents including guar, agar, methylcellulose and the like. In this method the liquid sample of the combining step can comprise nutrients and salts to permit the growth of a confluent lawn of bacteria and the test sample can be a dilution of an original sample containing bacteriophage. Preferably, the applying step comprises pouring the liquid sample onto the surface.

In one embodiment of this method the bacteriophage is capable of replicating in bacteria selected from the group of E. coli, Enterobacter, Salmonella, Staphylococci, Listeria and Mycobacterium.

The method of this invention employs a precipitable dye and a contrast-coloring dye. Preferably, the contrast-coloring dye is crystal violet. Also preferably, the precipitable dye is chromogenic and preferably forms a blue precipitate. In one embodiment, the surface with the liquid sample further comprises a pH sensitive dye and in a preferred embodiment, the pH sensitive dye is neutral red. In one embodiment the precipitable dye is 5-bromo-4-chloro-3-indolyl-β-D-glucuronic acid.

In another embodiment of this invention the surface with the liquid sample includes an inducer for the enzyme capable of enzymatically cleaving the precipitable dye. Preferably, the inducer is selected from the group of 1-O-methyl-β-D-glucuronide, isopropyl-β-D-thioglucuronic acid, isopropyl-β-D-thiogalactopyranoside, 3-O-methyl-α-D-glucopyranoside and 1-O-methyl-β-D-glucopyranoside. The inducer can be included in the surface, in the support, in the liquid sample or a combination thereof. In one embodiment, the enzyme cleaving the dye is selected from the group consisting of a β-D-glucuronidase, a β-D-galactosidase, an alkaline phosphatase and an acid phosphatase. Those of ordinary skill in the art will recognize that a particular inducer can by used to promote the production of a particular enzyme.

In one embodiment, the liquid sample comprises the contrast-coloring dye, the precipitable dye, and nutrients and salts for bacteria growth and in another embodiment, the semi-solid support comprises the contrast-coloring dye, the precipitable dye, and nutrients and salts for bacterial growth. In yet another embodiment, the hydratable solidifying support comprises the contrast-coloring dye, the precipitable dye, and nutrients and salts for bacterial growth.

Another aspect of this invention also relates to a method for performing a bacteriophage plaque assay, the improvement comprising detecting bacteriophage on a bacterial lawn on a support wherein the support comprises a contrast-coloring dye and a precipitable dye wherein a precipitate is formed from the enzymatic cleavage of the dye by an enzyme present in the bacterial lawn; and identifying plaques on the bacterial lawn.

In another aspect of this invention a method for detecting bacteriophage is disclosed comprising the steps of: combining bacteria and bacteriophage to form a liquid sample, wherein the concentration of bacteria is sufficient to form a bacterial lawn; adding the liquid sample to a well, the well comprising substantially vertical sides and a water-proof surface with a water-hydratable material dispersed thereon, wherein the water-hydratable material comprises a contrast-coloring dye and a precipitable dye and wherein the liquid sample in the well forms a support suitable for the formation and visualization of bacteriophage-derived plaques; and incubating the sample until at least one discrete plaque is visible.

In one embodiment, the bacteriophage is capable of growing in bacteria selected from the group of E. coli, Enterobacter, Salmonella, Staphylococci, Listeria and Mycobacterium. In another embodiment, the liquid sample of the combining step comprises nutrients and salts for bacterial growth. Alternatively, the hydratable material further comprises nutrients and salts for bacterial growth. In one embodiment, the contrast-coloring dye is crystal violet and in another, the precipitable dye produces a blue precipitate. In another preferred embodiment the hydratable material further comprises a pH sensitive dye and preferably, the pH sensitive dye is neutral red. In one embodiment, the precipitable dye is 5-bromo-4-chloro-3-indolyl-β-D-glucuronic acid.

The hydratable material of one embodiment can comprise an inducer for an enzyme capable of enzymatically cleaving the precipitable dye and a corresponding enzyme inducer selected from the group of 1-O-methyl-β-D-glucuronide, isopropyl-β-D-thioglucuronic acid, isopropyl-β-D-thiogalactopyranoside, 3-O-methyl-α-D-glucopyranoside and 1-O-methyl-β-D-glucopyranoside.

This invention also relates to a method for detecting bacteria comprising the steps of: contacting a sample comprising a first bacteria with bacteriophage in a liquid to form a liquid sample; removing bacteriophage not in contact with the first bacteria in the liquid sample; adding the bacteria of the contacting step to a water-proof surface, where the water-proof surface with liquid sample comprises a contrast-coloring dye and a precipitable dye; forming a bacterial lawn of a second bacteria, wherein the bacteriophage is capable of replicating in the bacteria of the bacterial lawn; and detecting a plurality of plaques, wherein a precipitate is formed in the plaques and the precipitate is the product of an enzymatic cleavage of the precipitable dye by an enzyme from the bacteria of the bacterial lawn and wherein detection of at least one plaque on the bacterial lawn indicates the presence of the first bacteria in the test sample. In one embodiment of this method, the bacteria of the contacting step is different from the bacteria of the bacterial lawn and preferably, the bacteriophage is capable of replicating in both the bacteria of the contacting step and the bacteria of the bacterial lawn.

In one embodiment of this method, the water-proof surface with liquid sample comprises a support for bacterial growth. In another embodiment, the liquid sample comprises a solidifiable support in liquid form and in a further embodiment the water-proof surface comprises a solidifiable support in liquid form and in another embodiment, the support comprises a hydratable solidifying support.

In one aspect of this method the contrast-coloring dye is crystal violet and in another the precipitable dye is 5-bromo-4-chloro-3-indolyl-β-D-glucuronic acid. In yet another aspect of this method the support further comprises neutral red and the surface with the liquid sample preferably includes an inducer for the enzyme of the detecting step. In one embodiment the inducer is selected from the group of 1-O-methyl-β-D-glucuronide, isopropyl-β-D-thioglucuronic acid, isopropyl-β-D-thiogalactopyranoside, 3-O-methyl-α-D-glucopyranoside and 1-O-methyl-β-D-glucopyranoside.

Preferably, the bacteriophage is capable of replicating in bacteria and selected bacteria that can be hosts for bacteriophage include those selected from the group of E. coli, Enterobacter, Salmonella, Staphylococci, Listeria and Mycobacterium.

In yet another aspect of this invention, the invention relates to a disposable device to detect bacteriophage comprising: at least one well comprising a water-proof surface and substantially vertical sides that form a well, the sides having a top and bottom, wherein the sides extend at least about 5 millimeters in height from the surface; and a hydratable material positioned on the water-proof surface, the material comprising a precipitable dye and a contrast-coloring dye wherein the contrast-coloring dye is capable of coloring the hydratable material and where the precipitable dye is capable of being cleaved by at least one enzyme from a bacteria to form precipitate at the site of a bacteriophage plaque.

The device preferably comprises a removable cover that is substantially impermeable to bacteria wherein the cover rests on top of the substantially vertical sides of the well. In one embodiment, the cover is transparent. Preferably, the water-proof surface is opaque and in one embodiment, the waterproof surface is white.

DETAILED DESCRIPTION OF THE PREFERRED EMBODIMENTS

Figure 1:
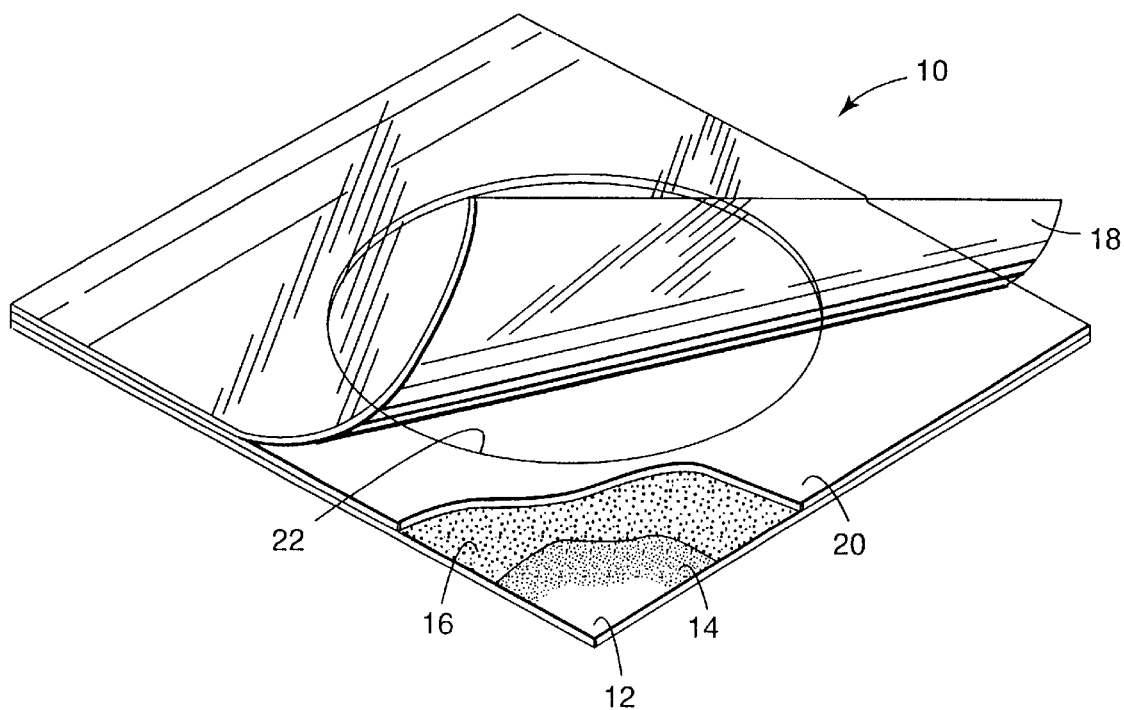
FIG. 1 is a top perspective view of a preferred device of the invention.

The present invention relates to a method for quantitating bacteriophage and to methods and devices to promote the visualization of viral plaques to facilitate virus quantitation. In one aspect of this invention, a method is disclosed for detecting bacteriophage on a solid or semi-solid support formed on a petri-plate or a dry-powder culture device such as thin film culture devices including "PETRI-FILM" -type devices. The invention teaches a method for improving visualization, and therefore, the improved quantitation of bacteriophage plaques using a combination of dyes.

The term "bacteriophage" is used herein to refer to viruses capable of infecting and replicating in bacteria. The term "plaque" is used herein to refer to areas of clearing or bacteriophage-derived discontinuity on a lawn of bacteria. The term "support" is used herein to refer to a solid or semi-solid medium capable of supporting bacterial growth in a way that permits the formation and visualization of viral plaques.

One aspect of this invention relates to a method for detecting bacteriophage plaques on a lawn of bacteria. The combination of at least one precipitable dye with at least one contrast-coloring dye was found to substantially improve the detection of bacteriophage plaques. More than one precipitable dye and more than one contrast-coloring dye can be used in this invention.

The term "contrast-coloring" dye refers to dyes that are capable of coloring at least the support, optionally, the bacteria itself, and permits growth of the lawn of bacteria and visualization of the virus plaques on the bacterial lawn. These contrast-coloring dyes do not react with their environment, that is, for example, they are not pH sensitive. Contrast-coloring dyes, as used in this invention, can include a variety of dyes. Examples of these dyes include, but are not limited to, crystal violet (C.I. 42555), rosaniline (C.I. 42510), methyl green (C.I. 42585), victoria blue (C.I. 42563), fast green (C.I. 42053), safranine O (C.I. 50240), trypan blue and a variety of food colorings known in the art. A preferred dye of this invention is crystal violet. Other suitable dyes meeting these characteristics are known and are detailed in a variety of texts, including, for example: Kiernan, J A, *Histological & Histochemical Methods: Theory & Practice,* 1981, Pergamon Press, New York.

Precipitable dyes of this invention are preferably at least partially soluble in water and serve as a substrate for a bacterial or viral enzyme to produce a colored precipitate. There are a number of different enzymes that have been identified that can enzymatically cleave the precipitable dyes of this invention. These enzymes include, but are not limited to, glycosidases, esterases, phosphatases and sulfatases. Suitable dyes include those that are metabolized by, or otherwise react with, bacteria enzymes of the bacterial lawn and in doing so create a colored precipitate that improves visualization of the bacteriophage plaques. These dyes are chromogenic, in that they produce a colored precipitate. Preferably, the colored precipitate is not white.

A variety of precipitable dyes are known that could be incorporated into the methods and devices of this invention, including indolyl-containing dyes including, but not limited to, 5-bromo-4-chloroindolyl phosphate or disodium salts of that compound, 5-bromo-4-chloroindolyl pyranoside or disodium salts of that compound, including 5-bromo-4-chloro-3 indolyl-β-D-glucuronic acid, 5-bromo-4-chloro-3-indoxyl-β-D-galactoside, 5-bromo-4-chloro-3-indolyl-β-D-glucopyranoside, 6-chloro-3-indolylphosphate, 5-bromo-6-chloro-3-indolylphosphate.

Preferably, the colored precipitate is blue. Substrates that create a blue colored precipitate include, but are not limited to, 5-bromo-4-chloro-3-indoxyl-N-acetyl-β-D-galactosaminide, 5-bromo-4-chloro-3-indoxyl-N-acetyl-β-D-glucosaminide, 5-bromo-4-chloro-3-indoxyl-β-D-cellobioside, 5-bromo-4-chloro-3-β-D-fucopyranoside, 5-bromo-4-chloro-3-indoxyl-α-D-galactopyranoside, 5-bromo-4-chloro-3-indoxyl-β-galactopyranoside, 5-bromo-4-chloro-3-indoxyl-α-D-glucopyranoside, 5-bromo-4-chloro-3-indoxyl-β-D-glucopyranoside, 5-bromo-4-chloro-3-indoxyl-β-D-glucuronic acid, cyclohexylammonium salt, 5-bromo-4-chloro-3-indoxyl-β-D-glucuronic acid, sodium salt, and 5-bromo-4--chloro-3-indoxyl-β-D-xylopyranoside.

The dyes can serve as substrates for particular enzymes present within certain types of bacteria. For example, blue-precipitate producing dyes that are substrates for esterases include, but are not limited to, 5-bromo-4-chloro-3-indoxyl butyrate, 5-bromo-4-chloro-3-indoxyl caprylate, and 5-bromo-4-chloro-3-indoxyl palmitate. Substrates for phosphatases include, but are not limited to, 5-bromo-4-chloro-3-indoxyl phosphate di(2-amino-2-methyl-1,3-propanediol) salt, 5-bromo-4-chloro-3-indoxyl phosphate disodium salt, 5-bromo-4-chloro-3-indoxyl phosphate and p-toluidine salt, 5-bromo-4-chloro-3-indoxyl phosphate and the potassium salt.

Chromogenic dyes that are substrates for glycosidases include, but are not limited to, 3-indoxyl-β-D-galactopyranoside, 3-indoxyl-β-D-glucopyranoside, 3-indoxyl-β-D-glucuronic acid cyclohexylammonium salt, and 3-indoxyl-β-D-glucuronic acid sodium salt. Other chromogenic substrates for phophatases include, but are not limited to, 3-indoxyl phosphate di(2-amino-2-methyl-1,3-propanediol) salt, and 3-indoxyl phosphate disodium salt, 3-indoxyl phosphate p-toluidine salt. Substrates for sulfatases include, but are not limited to, 3-indoxyl sulfate potassium salt.

Precipitable dyes that produce a magenta color for glycosidases, esterases, phosphatases and sulfatases include, but are not limited to 5-bromo-6-chloro-3-indoxyl-N-acetyl-β-D-glucosaminide, 5-bromo-6-chloro-3-indoxyl-β-D-galactopyranoside, 5-bromo-6-chloro-3-indoxyl-β-D-galactopyranoside, 5-bromo-6-chloro-3-indoxyl-β-D-glucopyranoside, and 5-bromo-6-chloro-3-indoxyl-β-glucuronic acid, cyclohexylammonium salt as substrates for glycosidases; 5-bromo-6-chloro-3-indoxyl butyrate, 5-bromo-6-chloro-3-indoxyl caprylate, and 5-bromo-6-chloro-3-indoxyl palmitate serve as substrates for esterases; 5-bromo-6-chloro-3-indoxyl phosphate, p-toluidine salt for phosphatases and 5-bromo-6-chloro-3-indoxyl sulfate, potassium salt serve as substrates for sulfatases.

Precipitable dyes that produce a salmon color for glycosidases, esterases and phosphatases include, but are not limited to, 6-chloro-3-indoxyl-β-galactopyranoside, 6-chloro-3-indoxyl-β-D-glucopyranoside, and 6-chloro-3-indoxyl-β-D-glucuronic acid, cyclohexylammonium salt for glycosidases; 6-chloro-3-indoxyl butyrate, 6-chloro-3-indoxyl caprylate, and 6-chloro-3-indoxyl palmitate for esterases; and, 6-chloro-3-indoxyl phosphate, p-toluidine salt for phosphatases.

Chromogenic substrates that produce a purple color include 5-iodo-3-indoxyl-β-D-galactopyranoside and chromogenic substrates that produce a green color include N-methyl-indoxyl-β-D-galactopyranoside.

Other precipitable dyes include 4,6-dichloro-N-acetylindol-3-ol, 6-chloroindolyl-β-D-galactoside pentaacetate, 6-chloroindolyl-β-D-galactoside, 6-chloroindoxy-1,3-diacetate, 5-chloro-2-carboxyphenylglycine sodium salt, 4-chloroanthranilic acid, methyl[6-chloro-N-acetylindol-3-yl-(2,3,4-tri-O-acetyl-β-D-glucopyranoside)]uronate, 6-chloroindolyl-β-D-glucopyranoside uronate monocyclohexylammonium salt, chloroindigos reported by Sadler et al., *J. Am Chem. Soc.* 78:1251–1255, 1956, as well as 4,6-dichloroindolyl-β-D-glucuronide, 6,7-dichloroindolyl-β-D-glucuronide, 6,7-dichloroindolyl-β-D-glucuronide, 4,6,7-trichloroindolyl-β-D-glucuronide, 4,6-dichloroindolyl-β-D-galactoside, 6,7-dichloroindolyl-β-D-galactoside, and 4,6,7-trichloroindolyl-β-D-galactoside. Those of ordinary skill in the art will be able to test these and/or other precipitable dyes in plaque assays to detect bacteriophage without undue experiment.

These compounds, and other precipitable dyes contemplated within the scope of this invention, are cleaved by bacterial enzymes to produce an insoluble precipitate. Preferably, the precipitable dyes are used in a final concentration from about 0.01 mg/ml to about 0.5 mg/ml and most preferably at about 0.02 mg/ml to about 0.2 mg/ml. Those skilled in the art will recognize that optimal concentration ranges used in the methods of this invention will depend on the type of precipitable dye used. Too low a concentration of dye will produce precipitate that cannot be visualized for plaque quantitation and too high a concentration of dye can be toxic to bacterial growth. Thus, the level of dye used can be determined without substantial experimentation.

The precipitable dye and the contrast-coloring dye are present in the support and this combination improves visualization of the plaques. As demonstrated in Example 1, when a precipitable dye alone was present in the support and available to the bacterial lawn, plaques could be seen, but the combination of the precipitable dye with the contrast-coloring dye produced striking results as compared to standard bacteriophage assays or assays employing a precipitable dye alone. Importantly, the improved plaque visualization can improve plaque quantitation and result in a better assessment of the amount of bacteriophage present in a particular samples.

The use of the dye combination of this invention can be incorporated into a variety of plaque-forming bacteriophage assays including standard petri-plate agar-based bacteriophage assays. A preferred use of the dye combination of this invention is the use of these dyes in dry powder or thin film culture systems.

The support of this invention refers to the agar, guar, methylcellulose or other solid or semi-solid gel-type support that permits the formation of a bacterial lawn and permits the visualization of virus plaques. The support can be formed by hydrating a water hydratable material that can then gel, where the water hydratable material is positioned on a water-proof surface or the support can be added as a solidifiable material applied in liquid form to a water-proof surface. Alternatively the support can be obtained as a combination of a water hydratable material positioned on a water-proof support and a solidifiable material applied in liquid form to the water-proof surface. Preferably, the support when solidified on the water-proof surface will contain the contrast-coloring dye or dyes, the precipitable dye or dyes and nutrients and salts to support bacterial growth.

Petri-plate agar-based bacteriophage assays are well known. Petri-plates in a variety of sizes, including multi-well culture plates, are well known in the art and available from suppliers such as Fisher Scientific (Pittsburgh. Pa.) and Nunc Nalgene (Rochester, N.Y.). In these assays, agar-containing petri-plates receive a top agar mixture that includes top agar, bacteria capable of supporting replication of a bacteriophage, and various dilutions of a test sample containing the bacteriophage. As the bacteriophage replicate, the bacteria lyse, forming plaques or areas of clearing or reduced turbidity on the confluent lawn of bacteria. The use of the dye combination of this invention results in improved visualization of the plaques. The dye combination can be added with the base agar layer on the petri-plate or the dye combination can be added to the top agar layer or a combination thereof.

In a preferred embodiment of this invention, the dye combination of this invention is incorporated into a dry powder culture system that is modified for bacteriophage quantitation. For example, a preferred device of this invention is provided in FIG. 1. A body member 10 includes a sheet having a water-proof surface 12 and dry powder 16 where dry powder 16 is fixed to, and covers at least, the growth region of the top face of surface 12 using, in one embodiment, an adhesive 14 or other means for adhering powder 16 to surface 12. A cover 18 for covering the powder and surface during shipping, storage, gel hydration and solidification, and bacteriophage incubation is also shown in FIG. 1 as being attached in a hinge-like fashion along one edge of body member 10. The cover is preferred to protect the cultures from dessication of the support and contamination by other bacteria and molds. Where a cover is not supplied with the device, those skilled in the art will recognize that some covering over the support will be useful to prevent contamination of the growth support during incubation.

Surface 12 is preferably a relatively stiff water-proof film made of a material, such as polyester, polypropylene or polystyrene that will not absorb or otherwise be adversely affected by water. Other suitable surfaces include paper having a polyethylene or other water-proof coating. An example of a suitable polyethylene-coated paper surface is "Schoeller Type MIL" photoprint paper (Schoeller Pulaski, New York). A preferred surface includes "MELINEX" (Dupont de Nemours) and other preferred surfaces of this invention are those water-proof surfaces having a white background. Polyester films of approximately 100 μm to about 180 μm thick, polypropylene films of about 100 μm to about 200 μm thick, and polystyrene films of about 300 μm to about 380 μm have been found to work well in the present invention. Another exemplary film is a transparent polyester film such as "SCOTCHPAR" (Minnesota Mining and Manufacturing, St. Paul, Minn.).

In one embodiment, surface 12 is coated on its exposed face with a layer of adhesive 14 that serves to hold the powder in place. Adhesive 14 should be water insoluble and should not inhibit the growth of the bacteria to be added to the device. In a preferred embodiment, the adhesive 14 is pressure-sensitive. However, heat-activated adhesives having a lower melting substance coated onto a higher melting substance can also be used. Water-activated adhesives such as mucilage are known and these too can be used in this invention.

Adhesive 14 can be coated onto surface 12 in a thickness preferably less than the diameter of the particles of the powdered gelling agent and/or nutrients. Sufficient adhesive is added to adhere the particles to the surface but not so much that the particles become completely embedded in the adhesive. A uniform monolayer of water soluble powder 16 is used having sufficient surface area exposed for hydration. Generally, an adhesive layer in the thickness range of 0.0002 to 0.0005 inch is suitable. As used herein, the term "powder" preferably designates a finely divided particulate material having an average diameter of less than about 400 micrometers.

The water insoluble adhesive is preferably a pressure-sensitive adhesive comprising a copolymer of an alkyl acrylate monomer and an alkyl amide monomer. Preferably, the weight ratio of alkyl acrylate monomer to alkyl amide monomer in these copolymers is from about 90:10 to about 99:1, more preferably, about 95:5 to about 98:2. In one embodiment, the preferred adhesive is a copolymer of isooctyl acrylate/acrylamide (in a mole ratio of 94/6). Other pressure sensitive adhesives can be used and include isooctylacrylate/acrylic acid (in a mole ratio of about 95/5 or about 94/6) and silicone rubber. Adhesives that turn milky upon exposure to water are less preferred unless they aid in the contrast between the bacterial lawn and the plaques.

One example of a method for preparing the water insoluble adhesive component of this invention is disclosed in U.S. Pat. No. 5,232,838 to Nelson et al. In general, an aqueous solution of a nonionic emulsifier and water is prepared. A previously prepared mixture of the alkyl acrylate and alkyl amid monomers in the desired weight ratios and a nonionic oleophilic polymerization initiator is then mixed and dispersed in the aqueous solution via the nonionic emulsifier. The mixing is carried out under homogenization conditions for about one minute to prepare an oil in water emulsion. The resulting oil in water emulsion is heated to induction temperature and stirred under nitrogen until polymerization occurs, as signaled by a reaction exotherm. Stirring is continued and if the resulting composition is to be coated directly, any additives such as nutrients and hydrophilic selective agents are added with stirring. Water is added or removed to reach a suitable coating viscosity. Typically, the adhesive particle diameter ranges from about 0.1 $\mu$m to about 0.9 $\mu$m and the filtered reaction mixture has a Brookfield viscosity of about 5 cps to about 15 cps. Appropriate adjustments to the pH of the adhesive composition are made, as needed, to insure that the adhesive composition is non-inhibitory to the growth of the bacterial host.

Adhesives are not required. For example, it is also possible to dissolve or suspend powder 16 in a liquid where the liquid is used to coat the surface and the coating is dried to provide a coating of dry powder on the surface. In these embodiments powder 16 can be in the form of a coating or a coating with discrete particulate. The powder 16 can comprise a dry gelling agent and/or nutrients in a uniform monolayer for easy hydration. The majority of the components making up powder 16 are preferably hydratable, that is, the addition of water to powder 16 reconstitutes the powder to create a suspension of the components of powder 16. The powder 16 can also include the dye combination of this invention; a precipitable dye and a contrast-coloring dye. The water solubility of the powder 16 employed in the devices of this invention may result, for example, from the inclusion of powders of an appropriate gelling agent. Suitable gelling agents for inclusion in powder 16 include both natural and synthetic gelling agents that form solutions in water at room temperature or up to about 40° C., depending on the temperature of the liquid sample that is added to the device. Gelling agents such as hydroxyethyl cellulose, carboxymethyl cellulose, polyacrylamide, locust bean gum and algin form solutions in water at room temperature and are suitable gelling agents for providing water hydratable powders or solids, according to this invention. Preferred gelling agents for powder 16 are guar gum and xanthan gum, these gelling agents are useful individually, or in combination with another gelling agent.

As indicated, powder 16 may comprise only a gelling agent. Where the device contains a powder comprising only a gelling agent, the end user combines the host bacteria with a sample comprising bacteriophage in a nutrient mixture suitable for the growth of the particular host bacteria. If nutrient is incorporated with the gelling agent, the dry powdered nutrients can be incorporated directly in the powder or suspended in a rapidly-evaporating liquid such as ethanol, or the like. In other instances, dry powdered nutrients can be suspended or dissolved in aqueous solutions. An aliquot of the liquid is added to the top face of surface 12 that has been previously coated with adhesive and gelling agent. The liquid is allowed to evaporate, under sterile condition, leaving ample nutrients along with the gelling agent.

A sufficient amount of gelling agent can be included in powder 16 so that a predetermined quantity of water or an aqueous sample, in general about 3 milliliters (ml) to about 5 ml placed into the well having a diameter of about 4 centimeters (cm) to about 6 cm, will form a gel of a viscosity that is suitable for the support of a bacterial lawn that permits the development of discrete quantifiable plaques. Gels having a viscosity suitable for the support of a bacterial lawn and the visualization of discrete viral plaques permit convenient handling and stacking of the device following hydration.

Powder 16 can also include dry growth media suitable for bacterial growth. Optionally, the media could include ingredients that favor the growth of one type, but not another type of, bacteria. Media or salts that favors the growth of a particular type of organism is known in the art and a variety of these media in dry form are available, for example, from Difco, Inc. (Detroit, Mich.). The dry medium is preferably water reconstitutable (i.e., hydratable) at temperatures of less than 42° C. For example, bile salts can be used to promote the growth of enteric bacteria.

A preferred coating mixture for powder 16 includes a gelling agent such as guar gum or xanthan gum, one or more nutrients suitable to support bacterial growth including, but not limited to yeast extract, peptone, sugars, suitable salts, and the like, as well as a contrast-coloring dye, a precipitable dye and optionally a pH sensitive dye, such as neutral red. A variety of nutrients suitable to support bacterial growth are known and these include bacto-yeast extract, bacto-tryptone, or the like. Those skilled in the art will recognize that a variety of other formulations could be used and that these do not detract from the scope of this invention. An exemplary powder 16 includes the powder composition provided in Example 1.

To form an adhered powder medium, a layer of cold-water soluble powder 16 is adhered, using adhesive 14, substantially uniformly to at least the growth region of adhesive layer 14. Powder 16 contains the components of the dry media. When gelling agent is included in powder 16, it is included in an amount such that a predetermined quantity of water or an aqueous sample (for example, at least about 5 ml, preferably, about 5 to about 10 ml based on the preferred embodiment, however larger volumes can be accommodated using larger well sizes and devices with larger dimensions) placed on the medium will form a reconstituted medium having a suitable viscosity to support a lawn of bacterial growth and the development of discrete viral plaques. Media of this viscosity allows convenient handling and stacking of the devices during incubation and provides for distinct plaque formation in the medium. The size of the powder particle can be used to control the coating weight per unit area.

The precipitable dye and the contrast-coloring dye can be included with powder 16. Alternatively, the precipitable dye and the contrast-coloring dye can be added at the time that the bacteriophage dilution and bacteria are added to the device. Where device 10 is not used and a standard petriplate bacteriophage assay is performed, the precipitable dye and the contrast coloring-dye can be included in the base agar, in the top agar, or a combination thereof.

The powder can also include other dyes, such as pH sensitive dyes where a pH indicator may be beneficial or otherwise enhance the visualization of the plaques. The powder can also include cross-linking agents or other reagents, such as fungicides or fungistats. Cross-linking agents can be added to create a stiffer gel, as needed. Suitable cross-linking agents do not substantially affect the growth of the bacteria and bacteriophage. Suitable types and amounts of cross-link-ing agents are easily selected by those skilled in the art. For example, with guar gum, crosslinking agents such as potassium tetraborate, aluminum salts, or calcium salts and divalent cations are suitable and can be added in effective amounts, e.g., less than about 1.0 percent by weight of dry medium, as long as the cross-linking agents do not inhibit the growth of the host bacterium or inhibit the adsorption of the bacteriophage to the host bacterium.

The assays of this invention may be designed to detect particular organisms. In one embodiment of assays of this type, a dilution of a known bacteriophage sample is added to unknown bacteria. The precipitable dye is selected based on its use as a substrate for an enzyme in a particular type of bacteria. Precipitable dyes specific for glycosidases, phosphatases, esterases, and the like are known and examples have been provided above. Not all bacteria have glycosidases, phosphatases, and esterases, hence the ability of a particular bacteriophage to infect and form plaques and the presence of a particular precipitate, for example, a particularly colored precipitate, in the plaque can be used to confirm the type of unknown bacteria.

In another embodiment of this invention, it is possible to include an inducer in powder 16, in the agar of a standard agar plate, or with the liquid sample comprising bacteriophage and bacteria. The inducer is specific for one or more proteins such as one or more enzymes in a bacteria and enhances the level of transcription and therefore the amount of protein (e.g., enzyme) in the bacteria. A variety of inducers are known in the art for a variety of enzymes. Exemplary inducers include, but are not limited to, 1-O-methyl-β-D-glucuronide or isopropyl-β-D-thioglucoronic acid for β-glucuronidase enzyme activity, isopropyl-β-D-thiogalactopyranoside for β-galactosidase enzyme activity, 3-O-methyl-α-D-glucopyranoside for α-glucosidase enzyme activity, and 1-O-methyl-β-D-glucopyranoside for β-glucosidase enzyme activity.

The device of this invention preferably includes a cover 18. In a preferred embodiment, the cover is a cover sheet, as illustrated in FIG. 1, that is adapted to cover at least the growth region of the medium. The cover 18 is preferably transparent to facilitate counting of bacteriophage plaques and is substantially impermeable to microorgansims and water vapor. Generally, the cover can be prepared from transparent materials including those used to make surface 12. The presently preferred material for the cover is polyester, for example, a transparent 4 mil (0.0 mm) polyester material.

Cover sheet material can be selected to provide the amount of oxygen transmission necessary for the type of bacterial host that is used. For example, polyester films have a low oxygen permeability (less than 0.78 g/100 cm$^2$/24 hours per 25 micrometer ($\mu$m) of thickness), and are suitable for growing anaerobic bacteria, or aerobic bacteria when utilized with air-permeable membranes, such as those described in U.S. Pat. No. 5,232,838 to Nelson et al. Alternatively, some forms of polyethylene have a relatively high oxygen permeability (approx. 78 g/100 cm$^2$/24 hours per 25 $\mu$m of thickness), and would be suitable for the growth of aerobic organisms, with or without the use of an air permeable membrane.

The device of the invention also includes a spacer 20 positioned between the surface 12 and the cover 18 to create a well or aperture 22 with substantially vertical sides that serves to define the growth region of the medium and confine the test sample to that part of the surface having powder 16. The spacer 20 of FIG. 1 is a spacer defining a circular well 22. The walls of the well 22 are substantially vertical and provide a well of predetermined size and shape and define the bacterial growth region of the device. Other well shapes could be used and those skilled in the art will recognize that the device of this invention could be configured with other spacer designs that would not detract from the scope of this invention.

The spacer 20 should be thick enough to form a well to hold the desired test sample volume. Preferably, the walls of the well are at least about 4 mm in height, and preferably about 5 mm to about 10 mm in height with the diameter or width of the well preferably at least about 5 cm. The spacer should be sufficiently thick to accommodate the entire test sample when it is placed in the well. Further, the spacer should be sufficiently thick that cover 18 does not contact the support containing the bacteria.

Preferably, the spacer 20 is prepared from closed cell polyethylene foam but a variety of materials that are hydrophobic (non-wetting), inert to microorganisms and preferably sterilizable can be used. Those skilled in the art will recognize that the thickness of the spacer can also vary with the size of the well.

To use the device of FIG. 1, cover sheet 18 is pulled back by the user and a predetermined quantity of liquid sample containing bacteriophage and a suitable bacterial host is added to surface 12 in well 22. A gelling agent present in the powder 16 is reconstituted or a gelling agent is present in the liquid sample so that the gelling agent creates a solid or semi-solid support that forms an area for bacterial growth. Where powder 16 does not include a gelling agent, the bacteria and bacteriophage can be added with a gelling agent such as agar, or the like, and added to the water-proof surface 12. Optionally, a gelling agent can be incorporated into powder 16 and a gelling agent, such as agar, for example, a top agar formulation (see Example 1), can be added to well 22. Where a gelling agent is used, the gelling agent is allowed to solidify and the device is incubated under conditions that promote the growth of the bacteria. The sample comprising bacteria and bacteriophage can be added simultaneously with the gelling agent or sequentially following addition of the gelling agent. The device is incubated for about 2 to about 24 hours and preferably between about 2 to about 10 hours, at least until plaques develop.

Where top agar is used, a preferred top agar comprises Bacto-Agar top agar (Becton & Dickinson Microbiology Systems, Cockeysville, Md.) containing nutrient broth (Becton & Dickinson Microbiology Systems) at a pH of about 7.2 to about 7.4. Other agar formulations and other solidifying agents can be used in this invention as well. The top agar is dispensed as a liquid into test tubes as described in Example 1. A sample of bacteria with a sample containing bacteriophage is added to the top agar. The mixture is agitated gently and the sample is poured onto powder 16. Once the top agar has reconstituted all or apart of powder 16 and solidified, the cover is replaced over the growth area and rests on spacer 20. The plates are incubated for a time and at a temperature to permit the bacterial lawn to form and for bacteriophage to replicate. The sample containing bacteriophage may be a dilution, for example, in media of the original bacteriophage-containing sample. Often serial 10-fold dilutions are prepared and aliquots from several dilutions are separately tested. The particular device with a number of discrete plaques, preferably greater than 10, is counted and the amount of bacteriophage is determined based on the dilution of original bacteriophage in the sample. For example, plaques are counted and the number of plaques is corrected for sample dilution to produce the number of plaques that would be present in a given volume of undiluted sample. Each plaque represents one infectious bacteriophage in the original inoculum; thus, the number of plaques corrected for dilution relates to the number of plaque forming units per volume.

The assay can be modified to identify plaques from a variety of bacteriophage using a variety of host bacteria. For example there are six major families of bacteriophages including Myoviridae (T-even bacteriophages), Styloviridae (Lambda bacteriophage groups), Podoviridae (T-7 and related bacteriophage), Microviridae (X174 group), Leviviridae (for example, *E coli* bacteriophage MS2) and Inoviridae as well as coliphages, in general, that can be detected using the methods of this invention. Other bacteriophage families include members of the Cystoviridae, Microviridae, and Siphoviridae families. A variety of bacteriophage that form plaques on *E. coli* are known. Bacteriophage that form plaques on Staphylococcus are known and these are listed in J. E. Blair and R. E. O. Williams. 1961. "Phage typing of Staphylococci" *Bull. W.H.O.* 24:771–784; that form plaques in Salmonella including bacteriophage SD11 and SD12 are provided by Stubbs, et al. 1994. *J. Clin. Microbiol.* 32:199 and Gershman M. 1977. *J. Clin. Miciobiol.* 5:302–314; bacteriophage that form plaques on Listeria are known and are provided for example by Van der Mee et al., 1995. *Appl. Environ. Microbiol.* 61:303; and bacteriophage that form plaques in Yersinia include K27 and are provided by Baker et al. 1982. *J. Clin. Microbiol.* 15:491–502. Bacteriophage of Pseudomonas include φ6 (available from the American Type Culture Collection (ATCC), Rockville, Md.), bacteriophage of *Salmonella choleiae* include P22 (available from ATCC), and bacteriophage from *Enterococcus faecalis* includes VD13 (also available from ATCC). In addition bacteriophage capable of replicating in Mycobacterium species are known as well.

In the experiments provided in Example 1, a sample of bacteriophage was added to *E. coli* in top agar and poured into the well formed by spacer 20 in device 10. Violet-blue colored plaques formed in about 2 hours with significant precipitate forming by 5 hours.

Importantly, as provided in Example 1, the plaques formed using the combination of dyes of this invention were more distinct than the plaques formed using precipitable dye alone. Plates incorporating the precipitable dye, without a contrast-coloring dye, as described in Example 1, produced clear plaques in the agar with the lawn of bacteria having a faint hue consistent with the color of the precipitable dye. In contrast, plaques formed on a support in the presence of a combination of precipitable dye and a contrast-coloring dye were colored according to the color of the contrast dye with heavy precipitate consistent with the color of the precipitable dye. The bacterial lawn had a very faint color of the precipitable dye. The contrast color combined with the presence of a precipitate in the plaque, made the plaque much easier to visualize than standard bacteriophage assays or bacteriophage assays using a precipitable dye alone.

The precipitable dye and contrast-coloring dye of this invention can be incorporated into one or more of the agar layers in a standard petri-plate type bacteriophage assay and the methods for performing petri-plate bacteriophage assays are known in the art.

Precipitable dyes (chromogenic substrates) have been used to identify bacteria. For example, U.S. Pat. No. 5,443,963 to Lund discloses the use of an indolylphosphate-containing dye that precipitates in the presence of an enzyme from Staphylococci. β-Galactosidase and β-glucuronidase substrates have been disclosed for the identification of coliforms and *E. coli*. For example, U.S. Pat. No. 5,358, 854 to Ferguson discloses the use of chromogenic dyes to detect coliforms and *E. coli*. Other patents disclosing the use of chromogenic dyes to identify bacteria include U.S. Pat. No. 5,364,767 to Flowers, U.S. Pat. No. 5,210,022 to Roth et al., and U.S. Pat. No. 5,393,662 to Roth et al. Surprisingly, and in contrast to the previously reported results, a confluent lawn of bacteria, did not produce substantial color. Only with bacterial lysis or bacterial degradation in the presence of bacteriophage, was a precipitate and substantial color present. This result is unexpected because, based on the patents to Flowers, Roth et al. and Ferguson, one would expect confluent color and hence that methods-employing precipitable dye and a lawn of bacteria would not be useful for quantitating bacteriophage. Moreover, with respect to the option of using inducers in the bacteriophage assays to stimulate enzyme production from the bacteria to increase the amount of precipitate that is formed, the presence of an inducer in this invention for bacteriophage quantitation did not create darkly colored colonies as might be expected based on the references cited above.

The assay and device of this invention are useful for bacteriophage quantitation in a variety of testing regimes. In addition to the use of the assay device of this invention in molecular biological techniques and the use of these assays to quantitate bacteriophage as a marker for bacterial food, water or milk contamination, the device can be used as part of a test protocol to determine the viral penetrability of a variety of substances including, but not limited to medical clothing, latex gloves, air-sterilizing filters, membrane filters, and the like. Example 2 details a method for assessing virus penetration in clothing using the methods of this invention.

The assay of this invention can also be used to detect bacteria. In these assays a sample comprising a test sample suspected of containing a particular type of bacteria is contacted with bacteriophage. Following an incubation period to permit adsorption of the bacteriophage to the bacteria, bacteriophage not in contact or not infecting the bacteria is removed. There are a number of methods to remove or separate free bacteriophage from bacteria at this stage. A method known in the art is to apply the sample to a centrifuge tube to either separate the bacteria by spinning the bacteria to the bottom of the tube or by separating the bacteria on a cushioning agent such as cellulose, other sugar solutions or other centrifuge density separation compounds known in the art. Rees et al. disclose other methods for separating or removing bacteriophage from a sample of bacteria including destroying, neutralizing or inactivating the extracellular bacteria and these methods are provided in U.S. Pat. No. 5,498,525. The bacteria sample is then preferably combined with a bacterial sample that is known to be capable of supporting replication of the bacteriophage. This bacteria sample is used to form a bacterial lawn. Plaques that form on the bacterial lawn on a support containing the precipitable dye or dyes of this invention and contrast-forming dye or dyes of this invention indicate the presence of the test or suspect bacteria in the test sample.

In another embodiment of this invention a kit is provided for the diagnosis of a particular type of bacteria based on the presence of a particular type of bacteriophage or a kit can be provided for the quantitation of a particular type of bacteriophage. The kit for bacterial identification preferably includes at least one culture well, such as the dry powder culture device provided in this invention, the dye combination according to this invention, either present in the dry powder of the coated film culture device (such as, for example, that provided in FIG. 1) or as an aliquot, either dry or liquid, to be added to the liquid sample comprising bacteriophage and bacteria prior to its application, host bacteria capable of supporting growth of the desired bacteriophage to be quantitated, and control bacteriophage.

All references, patents and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully practice the intended invention.

EXAMPLE 1

Bacteriophage Quantitation from a Test Sample

One side of a sheet of "MELINEX" film (duPont de Nemours, Bloomington, Del.) was coated with a solution of 3.0 g/l Bacto Yeast Extract (Difco), 7.0 g/l Bacto Peptone (Difco), 1.5 g/l Bacto Bile Salt No.3 (Difco), 10.0 g/l Bacto Lactose, 5.0 g/l NaCl, 0.042 g/l Neutral Red (Sigma, St. Louis, Mo.), 0.001 g/l Crystal Violet (Fisher Scientific), and 0.115 g/l 5-bromo-4-chloro-3-indolyl-β-D-glucuronic acid, cyclohexylammonium salt (BCIG, Biosynth International, Chicago, Ill.) in double distilled water. Prior to coating, the pH of the solution was adjusted to about 7.0 using $Na_2CO_3$. 10 g/l Guar (Meyhall Chemical AG, Kreuzlingen, Switzerland) was added and the solution was coated onto MELINEX and oven dried resulting in a coating of about 500 mg/24 $in^2$.

A spacer was made from a rectangular sheet of 8 cm×11 cm of 5 mm thick polystyrene foam with a centered circular well of about 5 cm diameter cut into it and attached by hand rolling pressure to a rectangular sheet of the above powder-coated film.

A top cover sheet was made from a stiff but flexible sheet of 4 mil (0.10 mm) thick sol-gel treated transparent polyester (SCOTHPAR polyethylene terephthalate film, No. FE 40492, 3M, St. Paul, Minn.) in a rectangular shape (8 cm×11 cm). The cover sheet was attached to the 8 cm width of the edge of the foam of the device by double coated pressure sensitive tape on a 0.7 cm section of the cover sheet. In use, the device was placed on a level surface and the top cover sheet folded back exposing the foam spacer and the well therein.

The bottom agar of standard petri-plates was prepared from a solution of about 15.0 g Bacto-Agar (Becton & Dickinson Microbiology Systems, Cockeysville, Md.), about 8.0 g nutrient broth (Becton & Dickinson Microbiology Systems, Cockeysville, Md.), and about 5.0 g potassium chloride in 1 liter of purified water. The pH of the agar was adjusted to about 7.2 to about 7.4 using 2.5 N sodium hydroxide. After autoclaving 1 ml of a 1 molar solution of calcium chloride was added.

Top agar for both the coated film devices and the standard petri-plates was prepared using about 7.0 g Bacto-Agar, about 8.0 g nutrient broth, and about 5.0 g. potassium chloride in a total volume of 1 liter of purified water. The pH of the agar was adjusted to about 7.2 to about 7.4 with 2.5 N NaOH. After autoclaving, 1.0 ml of a 1 molar solution of $CaCl_2$ was added to the top agar solution. A 2.5 ml sample of the sterile molten top agar was dispensed into sterile 16×125 mm polystyrene test tubes and held at about 45° C. An aliquot (100 µl) of an overnight culture of $E.$ $coli$ C (ATCC #13706) was added to each of the top agar tubes and held in the warm water bath. Depending on the assay, about 0.1 ml to about 1.0 ml of test sample containing dilutions of bacteriophage, PhiX174 (positive control, ATCC #13706-B 1) or no bacteriophage (negative control), was added to each of the tubes containing $E.$ $coli$. The contents of the tubes were mixed well and poured into the well of the coated film device or onto the petri-plates containing bottom agar. In one set of samples, top agar containing 1 mg/ml BCIG was poured onto the petri-plates and in another set of samples top agar containing 1 mg/ml BCIG and 1 mg/ml crystal violet was poured onto the petri-plates. The top agar was allowed to solidify and incubated at 37° C. for up to about 24 hours and examined at intervals over that period.

At two hours, plaques were visible as small blue tiny dots on the devices containing the coated film. Tiny plaques were also visible on the petri-plates, but no precipitate was observed. At three hours, small violet blue spotted plaques were present on the coated film while the plaques in the standard petri-plates were clear with a background of a blue hue. In contrast to the standard petri-plates containing precipitable dye alone, dry powder coated film devices comprising both the contrast-coloring dye and the precipitable dye contained distinct plaques in 3 hours. Plaque size continued to grow over the 24 hour period; however, the number of plaques at 6 hours was equivalent to the number of plaques counted at 24 hours. The plaques in the BCIG-containing petri-plates remained clear but agar plates with the precipitable dye in combination with the contrast-coloring dye created more distinctive plaques. The plaques in the petri-plates with the dye combination of this invention had a distinct colored edge. Where two or more plaques were in close proximity to one another petri-plates containing the dye combination of this invention had distinct edges that permitted easier quantitation. The powder coated film devices with the dye combination of this invention were significantly easier to quantitate than plates containing the precipitable dye alone. Bacteriophage calculations varied depending on the tests and the concentration of bacteriophage in the original sample to be tested. For assay optimization studies, plates were counted that contained 30–50 plaques per dish using a 10×100 mm petri-plate and this number of plaques was generally obtained using 0.1 ml of a $10^{-6}$ dilution of a standard bacteriophage test suspension containing at least about $1\times10^8$ plaque forming units/ml. Those of ordinary skill in the art will recognize that unknown test samples will contain an unknown bacteriophage concentration and that therefore a variety of dilutions of the unknown test sample are preferably be tested.

EXAMPLE 2

Method to Detect Virus Penetration Through a Material

Bacteriophage Phi-X174 approximates the size of Hepatitis C virus and is an accepted surrogate for Hepatitis B virus and the Human Immunodeficiency Virus (HIV) in the art (for example, see "Emergency Standard Test Method for Resistance of Protective Clothing Materials to Penetration by Blood-Borne Pathogens using Viral Penetration as a Test System", Designation ES 22-92, American Society for Testing and Materials, Philadelphia, Pa. 19103, pgs. 1–7).

Protective clothing material is contacted with a suspension of PhiX174 bacteriophage (American Type Culture Collection, Rockville, Md.) where the clothing is adjusted to a surface tension of 40 dynes/cm by adding 0.01% by volume surfactant-type Tween 80 for 5 min with no applied pressure, 1 min at 13.8 kPa (2.0 psig) and 54 additional minutes with no applied pressure or until liquid penetration is visually detected. The viewing side of the test material is rinsed with nutrient broth. This assay fluid is mixed with top agar containing *E. Coli,* as used in the assay of this invention. The mixture is poured into a well containing at least one precipitable dye and at least one contrast-coloring dye according to this invention. Viable virus present in the assay fluid is quantitated in the form of plaques using the device of this invention. The plaques are counted to determine the number of virus particles that penetrate the test material. Similar assays can be performed using latex glove material, air filters, membrane filters, and the like. These assays demonstrate that the bacteriophage assay and device of this invention are useful to detect or to assess the probability of viral penetration for a variety of mammalian viruses.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method for detecting bacteriophage comprising the steps of:
    combining a test sample comprising a suspect bacteriophage with bacteria capable of supporting replication of the bacteriophage to form a liquid sample;
    applying the liquid sample to a water-proof surface, wherein the water-proof surface with the liquid sample comprises a support for bacterial growth, and wherein the support includes at least one contrast-coloring dye, and at least one precipitable dye, and nutrients and salts capable of supporting growth of the bacteria forming a lawn of bacteria on the support; and
    detecting at least one plaque formed on the surface of the bacterial lawn, wherein a precipitate is formed in the at least one plaque and the precipitate is the product of an enzymatic cleavage of the precipitable dye by an enzyme from the bacteria of the bacterial lawn and wherein detection of at least one plaque on the bacterial lawn indicates the presence of the suspect bacteriophage in the test sample.

2. The method of claim 1, wherein the liquid sample comprises a solidifiable support in liquid form.

3. The method of claim 1, wherein the water-proof surface to which the liquid sample is applied comprises a hydratable solidifying support.

4. The method of claim 1, wherein the water-proof surface to which the liquid sample is applied comprises a semi-solid support.

5. The method of claim 1, wherein the support comprises agar.

6. The method of claim 1, wherein the bacteriophage is capable of replicating in bacteria selected from the group consisting of *E. coli,* Enterobacter, Salmonella, Staphylococci, Listeria and Mycobacterium.

7. The method of claim 1, wherein the liquid sample applied to the water-proof surface comprises nutrients and salts to permit the growth of a confluent lawn of bacteria.

8. The method of claim 1, wherein the test sample is a dilution of an original sample containing bacteriophage.

9. The method of claim 1, wherein the contrast-coloring dye is crystal violet.

10. The method of claim 1, wherein the precipitable dye is chromogenic.

11. The method of claim 10, wherein the precipitable dye produces a blue precipitate.

12. The method of claim 1, wherein the surface with the liquid sample further comprises a pH sensitive dye.

13. The method of claim 12, wherein the pH sensitive dye is neutral red.

14. The method of claim 1, wherein the surface with the liquid sample includes an inducer for the enzyme capable of enzymatically cleaving the precipitable dye.

15. The method of claim 14, wherein the inducer is selected from the group of 1-O-methyl-β-D-glucuronide, isopropyl-β-D-thioglucuronic acid, isopropyl-β-D-thiogalactopyranoside, 3-O-methyl-α-D-glucopyranoside and 1-O-methyl-β-D-glucopyranoside.

16. The method of claim 1, wherein the liquid sample comprises the contrast-coloring dye, the precipitable dye, and nutrients and salts for bacteria growth.

17. The method of claim 4, wherein the semi-solid support comprises the contrast-coloring dye, the precipitable dye, and nutrients and salts for bacterial growth.

18. The method of claim 3, wherein the hydratable solidifying support comprises the contrast-coloring dye, the precipitable dye, and nutrients and salts for bacterial growth.

19. The method of claim 10, wherein the precipitable dye is 5-bromo-4-chloro-3-indolyl-β-D-glucuronic acid.

20. The method of claim 1, wherein the liquid sample is poured onto the water-proof surface.

21. The method of claim 1, wherein the enzyme cleaving the dye is selected from the group consisting of a β-D-glucuronidase, a β-D-galactosidase, an alkaline phosphatase and an acid phosphatase.

22. A method for detecting bacteriophage comprising the steps of:
    combining a test sample comprising a suspect bacteriophage and bacteria capable of supporting replication of the bacteriophage to form a liquid sample, wherein the concentration of bacteria is sufficient to form a bacterial lawn;

adding the liquid sample to a well, the well comprising a water-proof surface with a water-hydratable material dispersed thereon, wherein the water-hydratable material comprises a contrast-coloring dye and a precipitable dye and wherein the liquid sample in the well comprises a support suitable for bacterial growth and for the formation and visualization of bacteriophage-derived plaques;

forming a lawn of bacteria on the water-hydratable material; and incubating the liquid sample until at least one discrete plaque is visible, wherein a precipitate is formed in the at least one plaque and the precipitate is the product of an enzymatic cleavage of the precipitable dye by an enzyme from the bacteria of the bacterial lawn and wherein detection of at least one plague on the bacterial lawn indicates the presence of the suspect bacteriophage in the test sample.

23. The method of claim 22, wherein the bacteriophage is capable of replicating in bacteria selected from the group consisting of *E. coli,* Enterobacter, Salmonella, Staphylococci, Listeria and Mycobacterium.

24. The method of claim 22, wherein the liquid sample applied to the water-proof surface comprises nutrients and salts to permit the growth of a confluent lawn of bacteria.

25. The method of claim 22, wherein the hydratable material further comprises nutrients and salts for bacterial growth.

26. The method of claim 22, wherein the contrast-coloring dye is crystal violet.

27. The method of claim 22, wherein the precipitable dye produces a blue precipitate.

28. The method of claim 22, wherein the hydratable material further comprises a pH sensitive dye.

29. The method of claim 28, wherein the pH sensitive dye is neutral red.

30. The method of claim 22, wherein the hydratable material further comprises an inducer for the enzyme capable of enzymatically cleaving the precipitable dye.

31. The method of claim 30, wherein the inducer is selected from the group of 1-O-methyl-β-D-glucuronide, isopropyl-β-D-thioglucuronic acid, isopropyl-β-D-thiogalactopyranoside, 3-O-methyl-α-D-glucopyranoside and 1-O-methyl-β-D-glucopyranoside.

32. The method of claim 22, wherein the precipitable dye is 5-bromo-4-chloro-3-indolyl-β-D-glucuronic acid.

33. A disposable device to detect bacteriophage comprising:

at least one well comprising a water-proof surface, the well having a depth of about at least 5 millimeters; and a hydratable material positioned on the water-proof surface, the material comprising a precipitable dye and a contrast-coloring dye wherein the contrast-coloring dye is capable of coloring the hydratable material and where the precipitable dye is capable of being cleaved by at least one enzyme from a bacteria to form precipitate at the sight of a bacteriophage plague, wherein the bacteriophage is capable of replicating in the bacteria.

34. The device of claim 33, further comprising the at least one well having substantially vertical sides and a removable cover that is substantially impermeable to bacteria on top of the substantially vertical sides.

35. The device of claim 33, wherein the cover is transparent.

36. The device of claim 33, wherein the water-proof surface is opaque.

37. The device of claim 33, wherein the water-proof surface is white.

* * * * *